United States Patent
Iketaki et al.

(10) Patent No.: US 7,551,350 B2
(45) Date of Patent: Jun. 23, 2009

(54) SUPER-RESOLUTION MICROSCOPE

(75) Inventors: Yoshinori Iketaki, Oume (JP); Takeshi Watanabe, Tama (JP); Masaaki Fujii, Yokohama (JP)

(73) Assignees: Olympus Corporation, Tokyo (JP); Tokyo Institute of Technology, Tokyo (JP)

( * ) Notice: Subject to any disclaimer, the term of this patent is extended or adjusted under 35 U.S.C. 154(b) by 0 days.

(21) Appl. No.: 11/659,525

(22) PCT Filed: Jul. 25, 2005

(86) PCT No.: PCT/JP2005/013584
§ 371 (c)(1),
(2), (4) Date: Feb. 5, 2007

(87) PCT Pub. No.: WO2006/016475
PCT Pub. Date: Feb. 16, 2006

(65) Prior Publication Data
US 2007/0291353 A1 Dec. 20, 2007

(30) Foreign Application Priority Data
Aug. 9, 2004 (JP) ............................. 2004-232230

(51) Int. Cl.
*G02B 21/06* (2006.01)
*G02B 21/00* (2006.01)
(52) U.S. Cl. ...................... 359/385; 359/368
(58) Field of Classification Search .......... 359/368–390
See application file for complete search history.

(56) References Cited

U.S. PATENT DOCUMENTS

| | | | | | |
|---|---|---|---|---|---|
| 5,866,911 | A | * | 2/1999 | Baer | 250/458.1 |
| 6,108,081 | A | * | 8/2000 | Holtom et al. | 356/301 |
| 6,184,535 | B1 | | 2/2001 | Kashima et al. | |
| 6,667,830 | B1 | * | 12/2003 | Iketaki et al. | 359/368 |
| 6,958,470 | B2 | * | 10/2005 | Hoffmann | 250/234 |
| 2001/0045529 | A1 | * | 11/2001 | Iketaki et al. | 250/493.1 |
| 2006/0290924 | A1 | * | 12/2006 | Iketaki et al. | 356/300 |

FOREIGN PATENT DOCUMENTS

| | | |
|---|---|---|
| JP | 8-184552 A | 7/1996 |
| JP | 11-95120 A | 4/1999 |
| JP | 2001-100102 A | 4/2001 |
| JP | 2001-272344 A | 10/2001 |

* cited by examiner

*Primary Examiner*—Thong Nguyen
(74) *Attorney, Agent, or Firm*—Frishauf, Holtz, Goodman & Chick, P.C.

(57) ABSTRACT

A super-resolution microscope includes an optical system for combining a part of a first coherent light from a first light source and a part of a second coherent light from a second light source and focusing the coherent lights onto a sample, scanning , unit for scanning the coherent lights, and a detecting unit for detecting an optical response signal from the sample. The microscope is configured so as to satisfy the following conditions:

$\sigma_{01} I p \tau \leq 1$, and $0.65(\lambda e/\lambda p) \leq \tau \sigma_{dip} Ie.$

4 Claims, 16 Drawing Sheets

SUPER-RESOLUTION MICROSCOPE

This application is a U.S. National Phase Application under 35 USC 371 of International Application PCT/JP2005/013584 filed Jul. 25, 2005.

TECHNICAL FIELD

The present invention relates to a microscope, and more specifically to a super-resolution microscope of high performance and high functional capability, realizing a high spatial resolution by irradiating a dyed sample with a plurality of lights having different wavelengths generated by a laser source of high performance.

BACKGROUND OF THE INVENTION

The technology of optical microscopes dates back centuries, and there have been developed various kinds of microscopes. In recent years, with advances in peripheral technologies including laser technology and electronic image processing technology, microscope systems of even higher functional capability have been developed.

Under such context, there has been proposed a microscope of high functional capability that can even perform a chemical analysis, as well as contrast control of an obtained image, using a double resonance absorption process caused by irradiating a sample with lights of different wavelengths (see, for example, Patent Document 1 listed below).

With this microscope, a specific molecule is selected using a double resonance absorption process, and an absorption and a fluorescence caused by a specific optical transition are observed. The principle used will be explained below with reference to FIGS. 12 to 15. FIG. 12 is a diagram of an electronic structure of valence orbits of a molecule contained in the sample. First, an electron in a valence orbit of a molecule in a ground state ($S_0$ state) shown in FIG. 12 is excited by a light having a wavelength $\lambda 1$ and thereby brought to a first electron-excited state ($S_1$ state) shown in FIG. 13. Then, the electron is excited by a light having another wavelength $\lambda 2$ in the same way and thereby brought to a second electron-excited state ($S_2$ state) shown in 14. In this excited state, the molecule emits fluorescence or phosphorescence and thereby returns to the ground state, as shown in FIG. 15.

In the microscopy using a double resonance absorption process, an image of absorption or luminescence is observed using the absorption process as shown in FIG. 13 or the luminescence of fluorescence or phosphorescence as shown in FIG. 15. In this microscopy method, first of all, a molecule contained in the sample is excited to the $S_1$ state as shown in FIG. 13 with a light, such as a laser beam, having the resonance wavelength $\lambda 1$. On this occasion, the number of molecules in the $S_1$ state per unit volume increases proportionally to the intensity of the irradiated light.

Here, the linear absorption coefficient is defined as a product of the absorption cross-sectional area per molecule and the number of molecules per unit volume. Thus, in a process of excitation as shown in FIG. 14, the linear absorption coefficient with respect to the resonance wavelength $\lambda 2$ of the second light depends on the intensity of the first light having the wavelength $\lambda 1$. In other words, the linear absorption coefficient with respect to the wavelength $\lambda 2$ can be controlled with the intensity of the light having the wavelength $\lambda 1$. This means that, by irradiating lights having the wavelength $\lambda 1$ and the wavelength $\lambda 2$, respectively, to the sample and capturing the transmitted image with respect to the wavelength $\lambda 2$, it is possible completely to control the contrast of the transmitted image with the light having the wavelength $\lambda 1$.

Further, if the returning process from the excited state with fluorescence or phosphorescence is possible in the excited state of FIG. 14, the intensity of luminescence is proportional to the number of molecules in the $S_1$ state. Consequently, it is possible to control the contrast of an image also in the case of application as a fluorescence microscope.

Further, in the microscopy using a double resonance absorption process, it is also possible to perform a chemical analysis, in addition to the above-mentioned control of the image contrast. More specifically, since the outermost valence orbit shown in FIG. 12 has an energy level inherent to each molecule, the wavelength $\lambda 1$ varies according to the kind of molecule and the wavelength $\lambda 2$ also becomes inherent to the molecule.

By using only a single wavelength in a conventional manner, it is also possible to observe an absorption image or a fluorescence image of a specific molecule to a certain degree. In this instance, however, an accurate identification of the chemical composition of the sample is not possible because some molecules generally have an overlapped range of the absorption wavelength.

On the contrary, in the microscopy using a double resonance absorption process, molecules are limited to those that absorb a light or produce a luminescence with two wavelengths $\lambda 1$ and $\lambda 2$, and it is thus possible to achieve even more accurate identification of chemical composition of the sample, as compared to the prior art. Further, when exciting a valence electron, since only a light having a certain electric field vector relative to the axis of the molecule is strongly absorbed, it is possible to identify even the orientation of the same molecule by suitably determining the polarizing directions of the lights having the wavelengths $\lambda 1$ and $\lambda 2$ and capturing the absorption or fluorescence image.

Furthermore, a fluorescence microscope using a double resonance absorption process and having a spatial resolution higher than the diffraction limit has recently been proposed (see, for example, Patent Document 2 listed below).

FIG. 16 is a schematic diagram of a double resonance absorption process in a molecule, in which the molecule in the ground state $S_0$ is excited to the first electron-excited state $S_1$ with a light having the wavelength $\lambda 1$ and further to the second electron-excited state $S_2$ with a light having the wavelength $\lambda 2$. In addition, FIG. 16 illustrates that fluorescence from $S_2$ state is extremely weak for certain type of molecule.

In the case of a molecule having an optical property as shown in FIG. 16, a phenomenon of significant interest can be observed. FIG. 17 is a schematic diagram of a double resonance absorption process similar to FIG. 16, in which the horizontal axis (X axis) represents a stretch of spatial distance, which is divided into spatial regions $A_1$ exposed to the light of the wavelength $\lambda 2$ and a spatial region $A_0$ not exposed to the light of the wavelength $\lambda 2$.

In FIG. 17, a great number of molecules are excited to $S_1$ state by the light of the wavelength $\lambda 1$ in the spatial region $A_0$, so that a fluorescence of a wavelength $\lambda 3$ from the spatial region $A_0$ is observed. In the spatial regions $A_1$, on the other hand, due to the light of the wavelength $\lambda 2$ being irradiated, most of the molecules in $S_1$ state are instantaneously excited to the higher energy level $S_2$ state, so that there exist no molecules in $S_1$ state. Such a phenomenon has been confirmed as to some molecules. Since fluorescence of the wavelength λ3 is completely eliminated in the spatial region $A_1$, and as there is no fluorescence from $S_2$ state, fluorescence is entirely inhibited in the spatial regions $A_1$ (fluorescence inhibiting effect). Thus, there is produced fluorescence only from the spatial region $A_0$.

Considering the present application field of a microscope, those phenomena have an extremely important meaning. In other words, with the conventional scanning laser microscope or the like, wherein laser beam is focused into a micro beam by a condenser lens to scan over a sample to be observed, the size of the micro beam is limited within a diffraction limit determined by the numerical aperture of the condenser lens and the wavelength of the laser beam, so that a spatial resolution higher than the diffraction limit cannot theoretically be expected.

In the case of FIG. 17, however, a spatial resolution can substantially be improved because, as to the irradiated region of a light of the wavelength λ1, for example, a fluorescence region can be made smaller than the diffraction limit determined by the numerical aperture of condenser lens and the wavelength of the light by suitably and spatially combining two kinds of lights, i.e., a light of the wavelength λ1 and a light of the wavelength λ2. In the following description, the light of the wavelength λ1 is referred to as a "pump light", and the light of the wavelength λ2 is referred to as an "erase light". Therefore, by applying this theory, it is possible to realize a super-resolution microscope, for example a super-resolution fluorescence microscope, having a higher resolution than a diffraction limit, and using the double resonance absorption process.

Patent Document 1: JP 08-184552 A

Patent Document 2: JP 2001-100102 A

DISCLOSURE OF THE INVENTION

In a super-resolution fluorescence microscope, for effectively performing its capability, it is required to cautiously optimize the irradiating intensity of a pump light and an erase light with sufficient consideration on the optical property of a molecule. The light intensity of the erase light, in particular, has a significant influence over realization of a super-resolution. In addition, according to the experimental review by the present inventors, a two-dimensional point spread function obtained by the super-resolution microscope, i.e., the intensity profile of fluoresce spots, proved to be significantly different from that of the conventional optical microscopes.

As the most fundamental physical quantity for evaluating the optical capability of an optical microscope, there is a point spread function (PSF). If this quantity is elucidated, an optical transfer function (OTF) can be calculated, which is indispensable for the total evaluation of two point resolution that determines the resolution of a microscope or an image quality.

In general microscope systems, there is used an optical system in which lenses with circular openings, apertures, and the like are combined. The PSF of the optical systems of the kind is given as well-known Fraunhofer diffraction image in the case of a circular aperture. The intensity within the image surface at a distance (r) from the optical axis, i.e., a point spread function (H(r)), can be expressed by Formula (1) as follows, wherein λp is the wavelength of the light source is and NA is the numerical aperture of the optical system.

[Formula 1]

$$H(r) = C_{P0}\left[\frac{2J_1(k_p NAr)}{k_p NAr}\right]^2 \quad (1)$$

$$k_p = \frac{2\pi}{\lambda_p} NAr$$

Here, $(J_1(z))$ is a first order of Bessel function, $(C_{po})$ is a center intensity and $k_p$ is a wave number of the light source. For most microscope systems, image formational theory based on the PSF of the Formula (1) is constructed and used for evaluating the performance of the system. In the case of a fluorescence microscope, its performance is similarly evaluated based on the Formula (1), assuming that the fluorescence intensity from the sample is proportional to the irradiating intensity of the excitation light source.

In the case of a super-resolution microscope, however, there exists no proportionality between the irradiating intensity of the light source and the fluorescence intensity, because the sample resonantly absorbs two lights of different wavelengths.

It is reported that, even if the irradiation intensity of the pump light is constant, the obtained fluorescence intensity is nonlinearly attenuated if the irradiating intensity of erase light is increased. Such an optical response characteristic obviously has a strong influence over the PSF. As a matter of fact, according to a recent report (Optics Express, Vol. 11, No. 24, p 3271-3276), the PSF of a super-resolution microscope exhibits a profile similar to Lorentzian type, which is significantly different from the intensity distribution of Formula (1), and which rarely appears in general optical systems.

For these reasons, the optimal conditions of the pump light and the erase light for realizing a super-resolution microscope had been unclear, with the result that selection of the light source for the pump light and the erase light had been difficult.

Therefore, in view of these circumstances, it is an object of the present invention to provide an super-resolution microscope, wherein the light source of pump light and the erase light can be selected easily and the super-resolution can be reliably achieved with a simple and inexpensive arrangement.

To this end, a first aspect of the invention resides in a super-resolution microscope, which comprises: a first light source for irradiating a first coherent light, with respect to a sample containing a molecule with at least three electronic states including a ground state, so as to excite the sample from the ground state to a first electron-excited state having an excited lifetime τ; a second light source for irradiating a second coherent light to the sample so as to excite the sample from the first electron-excited state to a second electron-excited state having a higher energy level than the first electron-excited state; optical systems for combining a part of the first coherent light and a part of the second coherent light and focusing the coherent lights onto the sample; a scanning unit for scanning the sample by relatively moving the lights focused by the optical systems; and a detecting unit for detecting an optical response signal generated by the sample as a result of the irradiation from the optical systems; wherein the super-resolution microscope is configured so as to satisfy the following conditions:

$\sigma_{01} Ip\tau \leq 1$, and $0.65(\lambda e/\lambda p) \leq \tau \sigma_{dip} Ie$ where $\lambda p$ is a wavelength of the first coherent light, $\lambda e$ is a wavelength of the second coherent light, $\tau$ is the excited lifetime in which the molecule is excited by the first coherent light from the ground state to the first electron-excited state, Ip is a maximum photon flux on a sample surface of the first coherent light, Ie is a maximum photon flux on a sample surface of the second coherent light, $\sigma_{01}$ is an absorption cross-sectional area when the molecule is exited from the ground state to the first electron-excited state, and $\sigma_{dip}$ is a fluorescence suppression cross-sectional area.

A second aspect of the invention resides in an super-resolution microscope, wherein it is configured so as to further satisfy the following condition:

$\tau\sigma_{dip}Ie \leq 1$.

According to the present invention, by configuring the microscope to satisfy the above-mentioned specified conditions, a super-resolution microscope can easily be realized, in which the light source of pump light and erase light can be selected easily, a continuous wave laser having high reliability can be used instead of a short pulse laser source, for example, which is difficult to handle, and a super-resolution can be reliably achieved with a simple and inexpensive arrangement.

BEST MODE FOR CARRYING OUT THE INVENTION

An embodiment of a super-resolution microscope according to the present invention will be explained below.

Figure 1:
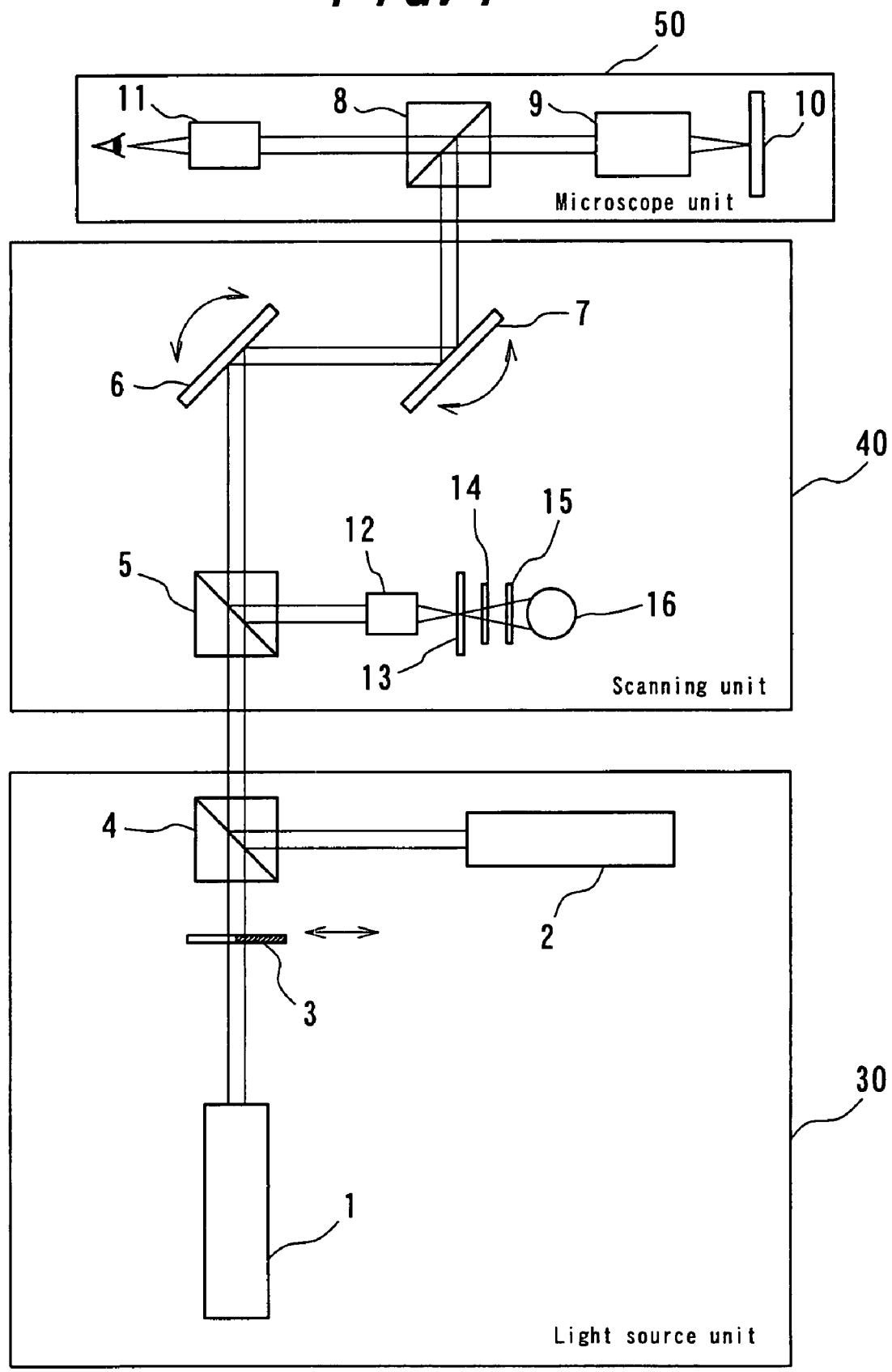
FIG. 1 shows a configuration of a super-resolution microscope system according to an embodiment of the present invention.

FIG. 1 shows a configuration of a super-resolution microscope system of according to an embodiment of the present invention. This super-resolution microscope is supposed to be an ordinary laser scanning type fluorescence microscope, and comprised of three independent units, i.e., a light source unit 30, a scanning unit 40 and a microscope unit 50.

Figure 2:
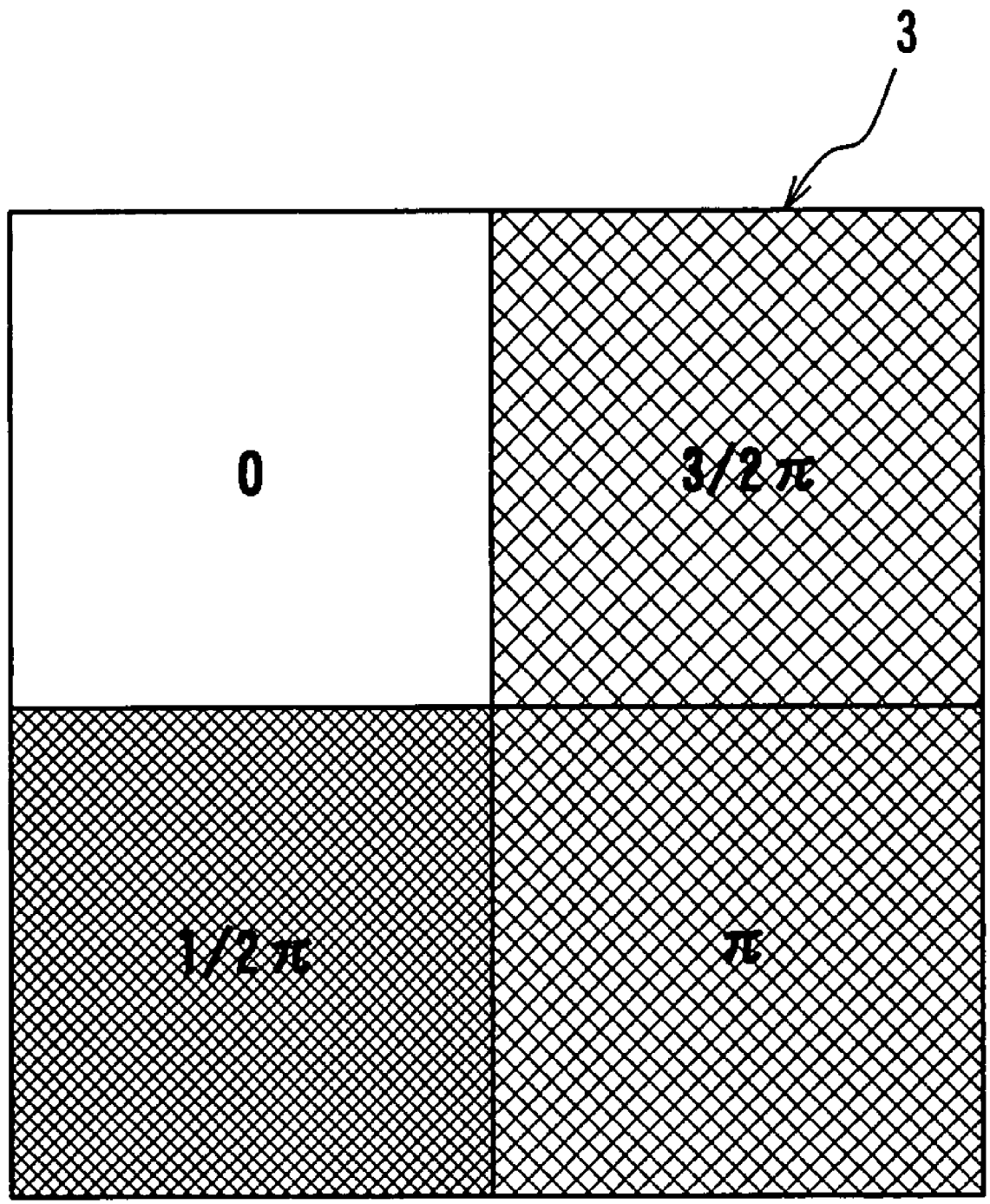
FIG. 2 shows a configuration of the phase plate shown in FIG. 1.

The light source unit 30 comprises a first light source, for example an LD-excited type mode-locked Nd:YAG laser 2 irradiating a pump light having a wavelength 532 nm as a first coherent light, a second light source, for example a Kr laser 1 irradiating an erase light having a wavelength 647 nm as a second coherent light, a phase plate 3 for spatially modulating the erase light, and a beam combiner 4 for combining the erase light and the pump light. On the surface of the phase plate 3, an optical thin film is evaporated for reversing the phase of the erase-light transmitted at symmetrical positions with reference to the optical axis, as shown in FIG. 2. In FIG. 2, the phase plate has four (4) independent areas around the optical axis, each having a phase shifted relative to the other by ¼ with reference to the wavelength of the erase light. By focusing the light transmitted through this phase plate 3, the electric field is cancelled on the optical axis so as to generate an erase light of hollow shape.

The scanning unit 40 is configured so that the pump light and the erase light generated by the light source unit 30 and sharing the identical optical axis are transmitted through the half mirror 5, subjected to two-dimensional oscillating-scanning by galvanometer mirrors 6 and 7 as a scanning means, and then irradiated to the microscope unit 50 to be described hereinafter. In addition, the fluorescence detected by the microscope unit 50 is branched by the half mirror 5 after passing back the approaching route, and the branched fluorescence is transmitted through a projector lens 12, a pin hole 13 and notch filters 14 and 15, and subsequently received by a photoelectron multiplier 16 as a detecting means. In order to simplify the illustration, the galvanometer mirrors 6 and 7 are shown in FIG. 1 as being capable of oscillating only within the same plane. The notch filters 14 and 15 serve to remove the pump light and the erase light which have been mixed in the fluorescence. Moreover, the pin hole 13 is an important optical element constituting a confocal optical system, and serve to only transmit the fluorescence emitted at a specific fault plane of the observed sample.

The microscope unit 50 comprises an ordinary fluorescence microscope, which is configured so that the pump light and the erase light irradiated from the scanning unit 40 are reflected by a half mirror 8 and focused by an objective lens 9 onto an observation sample 10 containing a molecule with at least three electronic states including a ground state. A fluorescence is thus emitted from the observed sample 10, and is returned back to the scanning unit 40 after being collimated by the objective lens 9 and reflected by the half mirror 8, while a part of the fluorescence transmitting the half mirror 8 is simultaneously guided to an ocular lens 11 so that it can be visually observed as a fluorescence image.

The phase plate 3, the beam combiner 4 and the objective lens 9 as a whole constitute an optical system for combining a part of the pump light and the erase light and focusing the combined light onto the observation sample 10.

The present embodiment is configured, as to the super-resolution microscope shown in FIG. 1, so that following conditions are satisfied:

$\sigma_{01} I p \tau \leq 1$, and $0.65(\lambda e/\lambda p) \leq \tau \sigma_{dip} Ie$, more preferably $\tau \sigma_{dip} Ie \leq 1$ where λp is the wavelength of the pump light for exciting the molecule contained in the observation sample 10 from a ground state to a first electron-excited state having an excited lifetime τ, λe is the wavelength of the erase light for exciting the molecule from the first electron-excited state to a second electron-excited state having even higher energy level than the first electron-excited state, Ip is the maximum photon flux on the observed sample surface of the pump light, Ie is the maximum photon flux on the observed sample surface of the erase light, $\sigma_{01}$, is the absorption cross-sectional area when the molecule is exited from the ground state to the first electron-excited state, and $\sigma_{dip}$ is the fluorescence suppression cross-sectional area.

With such configuration of the super-resolution microscope, on the focal point on the observation sample 10, fluorescence is inhibited at all the spots except the proximity of the optical axis where the intensity of the erase light becomes zero. As a result, there are observed only fluorescence labeler molecules existing within an area (Δ<0.61·λ1/NA, where NA is the numerical aperture of the objective lens 9), which is smaller than the dispersion of the pump light, so as to achieve a super-resolution. Therefore, by measuring the fluorescence signal while scanning the pump light and the erase light with scanning unit 40, it is possible to obtain a two-dimensional fluorescence image with a super-resolution.

In the following, explanation is made of the grounds for the above-mentioned configuration, i.e., the principle of the super-resolution microscope according to the present invention.

The PSF in the super-resolution microscopy is determined by the intensity distribution (H(r)) of the pump light and the intensity distribution (G(r)) of the erase light on the sample surface, and the fluorescence inhibiting characteristic of the sample at the moment of simultaneous irradiation of the pump light and erase light, i.e., the dip ratio (P(Ie)). Here, Ie represents the photon flux of the erase light, and the dip ratio concretely represents the ratio of fluorescence intensity between the case where the erase light is not irradiated and the case where the erase light is irradiated. As the fluorescence intensity is proportional to H(r) in case only the pump light is irradiated, the fluorescence intensity profile (F(r)) in the case of simultaneous irradiation of the erase light with the pump light is represented as a product of the fluorescence inhibiting characteristic and the intensity of the pump light, which is expressed by Formula (2) as follows.

[Formula 2]

$$F(r)=P[G(r)]H(r) \quad (2)$$

Figure 3:
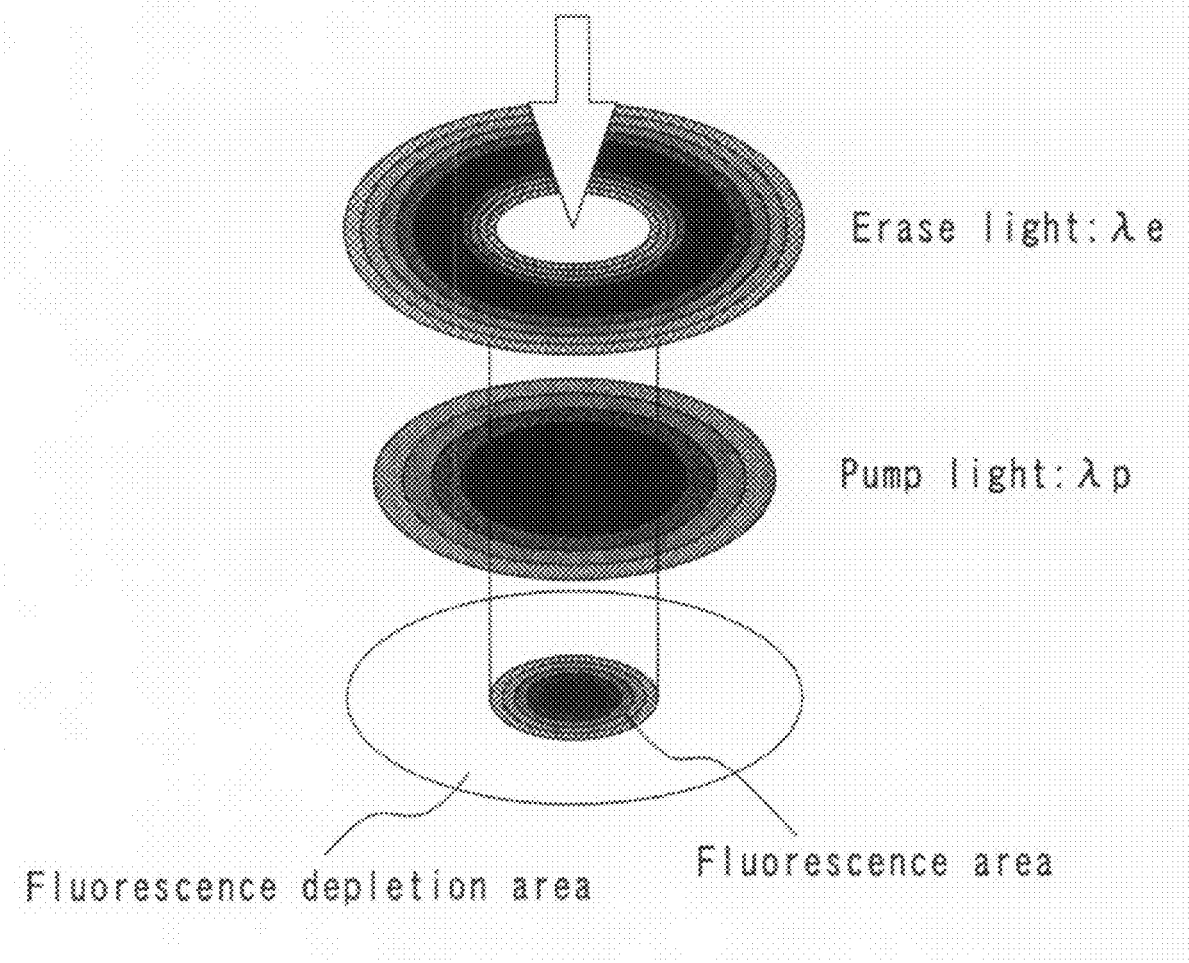
FIG. 3 schematically shows the beam profiles of the erase light and pump light, and the fluorescence area and a fluorescence depletion area on the sample surface.
Figure 4:
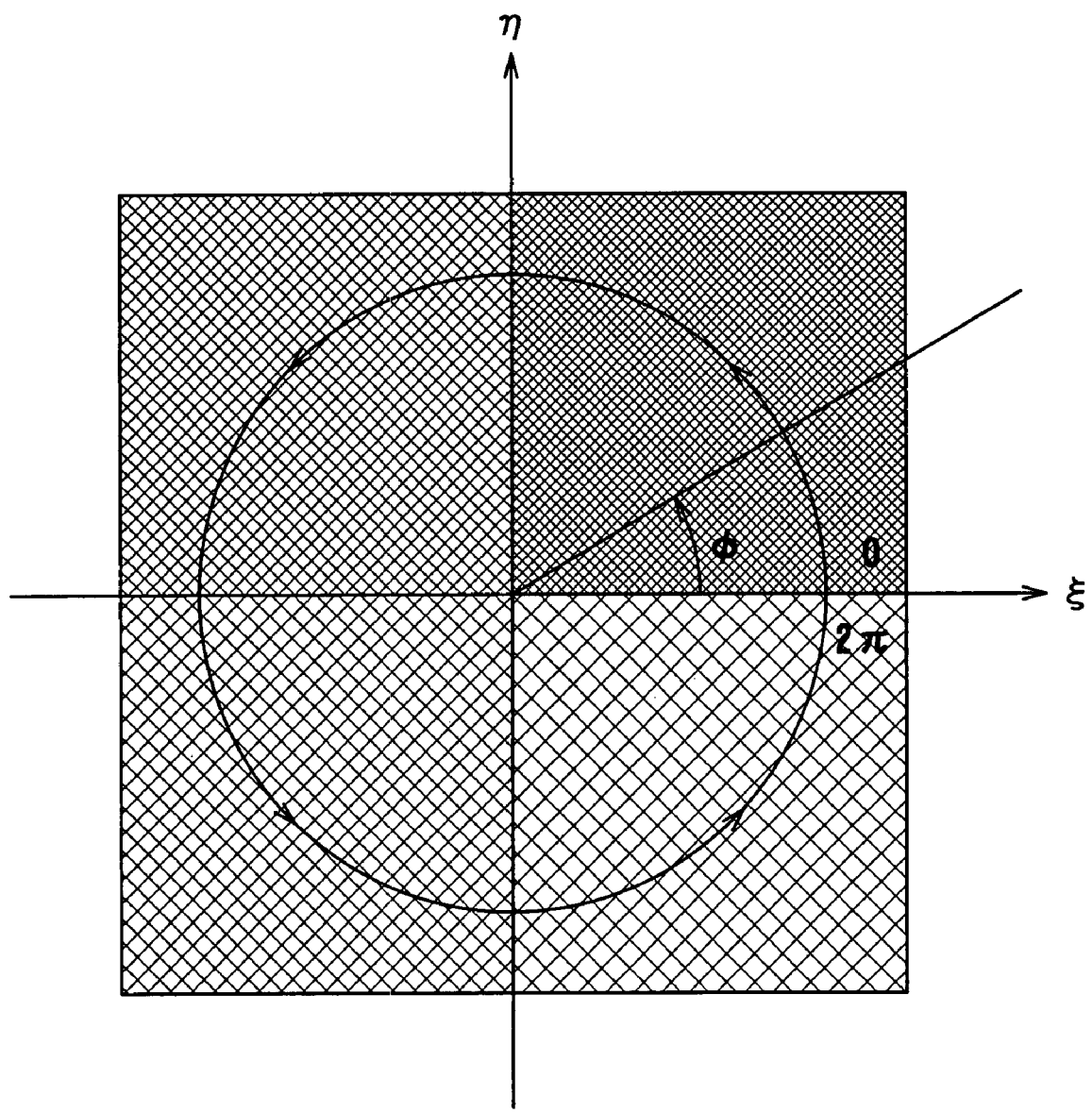
FIG. 4 shows the phase distribution on the beam cross-section of the erase light.

In a practical super-resolution microscopy, a hollow primary Bessel beam having no light intensity along the optical axis as shown in FIG. 3 is used as an erase light. Here, if the objective lens of the microscope is an aplanatic optical system, the shape of the pump light H(r) is given by Formula (1). On the other hand, the Bessel beam used as the erase light has a phase distribution as shown in FIG. 4, wherein, at the beam cross-section (pupil plane), the phase continuously changes from 0 to 2π around the optical axis of the beam. Therefore, the phase of the erase light differs by n with respect to the optical axis in all the radial directions, with the result that the intensity of the electric field is canceled along the optical axis after the lights have been focused, so that its intensity distribution is expressed by Formula (3) as follows, with the maximum beam intensity value ($C_{e0}$).

[Formula 3]

$$G(r) = 15.38 C_{e0} \left| \frac{2}{(k_e NAr)^2} \sum_{n=1}^{\infty} J_{2n+1}(k_e NAr) + \frac{1}{k_e} J_2(k_e NAr) \right|^2 \quad (3)$$

$$ke = \frac{2\pi}{\lambda_e} NAr$$

Figure 5:
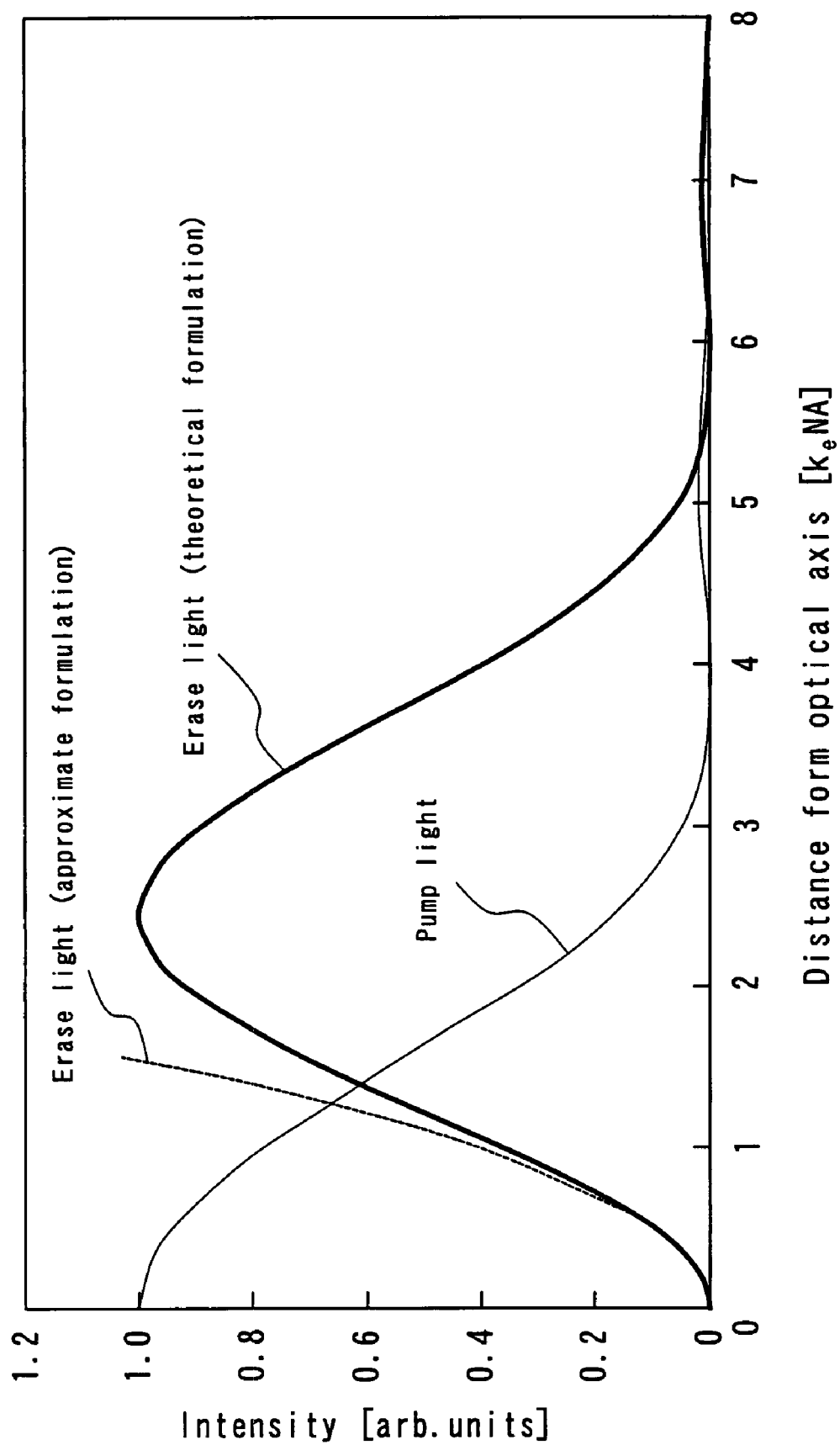
FIG. 5 shows a intensity distributions of a pump light and an erase light on the sample surface.

Here, $\lambda_e$ and $k_e$ represent the wavelength and the wave number of the erase light, respectively. In addition, Jn(z) is a Bessel function of $n^{th}$ order where n≧2, which is not less than $r^2$, so that it can be readily understood that G(0)=0 if r=0. The heavy line in FIG. 5 is obtained by plotting Formula (3) with configuring its maximum value as 1 and λ/NA as 1, so that a hollow profile can be obtained having an intensity of 0 where r=0, which is ideal as an erase light. In addition, the beam profile in the case where a pump light having a uniform wave surface is focused is also plotted in FIG. 5 with thin line, for the purpose of comparison. As can be appreciated from FIG. 5, if a hollow profile ideal as an erase light is obtained, the fluorescence can be effectively inhibited at the surrounding of the doughnut without losing the fluorescence intensity around the center, thereby forming a fluorescence spot that is smaller than the diffraction limit.

Figure 6:
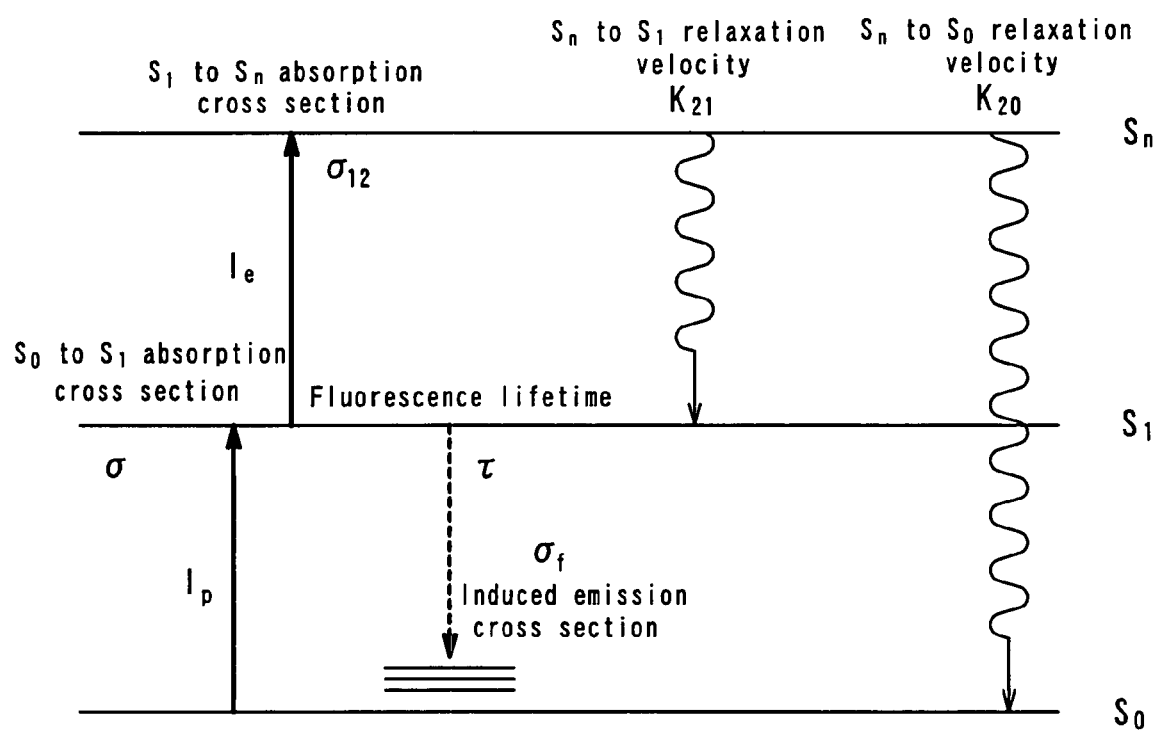
FIG. 6 shows an excitation diagram of a two-wavelength fluorescence dip spectroscopy.

The dip ratio also is an important factor for determining the exhibition degree of the super-resolution, as well as the beam shape of the erase light. The drip ratio is an optical response characteristic inherent to the molecule, which is caused by its molecular structure. The excitation diagram of the two-wavelength fluorescence Dip spectroscopy is shown in FIG. 6. Generally, as shown in FIG. 6, when a molecule in the ground state ($S_0$ state) is excited by the pump light to the first electron-excited state ($S_1$ state), it emits a fluorescence from the first electron-excited state and is relaxed to the ground state. Here, by irradiating the erase light, the molecule is excited to a higher quantum state ($S_n$), and undergoes a non-radiative relaxation to $S_0$ state or Tm triplet state. If the wavelength of the erase light is overlapped with the wavelength range of the fluorescence, stimulation emission process also occurs. Thus, the intensity of the fluorescence is reduced when the erase light is irradiated, and this change is observed as a dip (Dip).

Since the intensity of the fluorescence is generally proportional to the population in the $S_1$ state, the dip ratio can be analyzed by obtaining the population. More specifically, as the observed intensity of the fluorescence is an integrated quantity of the population with respect to the observation time (T), the dip ratio P(Ie) is expressed by Formula (4), as follows.

[Formula 4]

$$P(I_e) = \frac{\int_0^T n_1(t, I_e)}{\int_0^T n_1(t, 0)} dt, \quad (4)$$

Here, $n_1$(t,Ie) is the population in the $S_1$ state, and it is represented as a function of the photon flux of the erase light and the observation time. In addition, the population $n_1$(t,Ie) is determined by a three level rate equation with the populations in the $S_0$($n_0$(t,Ie)) state and $S_n$ state ($n_2$(t,Ie)) being added to that of $S_1$ state.

[Formula 5]

$$\begin{bmatrix} \frac{dn_0(t, I_e)}{dt} \\ \frac{dn_1(t, I_e)}{dt} \\ \frac{dn_2(t, I_e)}{dt} \end{bmatrix} = \begin{bmatrix} -\sigma_{01}I_p & \frac{1}{\tau} + \sigma_f I_e & k_{20} \\ \sigma_{01}I_p & -\frac{1}{\tau} - \sigma_f I_e - \sigma_{12}I_e & k_{21} \\ 0 & \sigma_{12}I_e & -k_{21} - k_{20} \end{bmatrix} \begin{bmatrix} n_0(t, I_e) \\ n_1(t, I_e) \\ n_2(t, I_e) \end{bmatrix}, \quad (5)$$

The spectral parameters used here are shown in FIG. 6. This rate equation is a first order liner differential equation, and has generally solutions of the following forms.

[Formula 6]

$n_0(t,I_e) = D_{11}e^{\gamma_1 t} + D_{12}e^{\gamma_2 t} + D_{13}e^{\gamma_3 t}$ $n_1(t,I_e) = D_{21}e^{\gamma_1 t} + D_{22}e^{\gamma_2 t} + D_{23}e^{\gamma_3 t}$, $n_2(t,I_e) = D_{31}e^{\gamma_1 t} + D_{32}e^{\gamma_2 t} + D_{33}e^{\gamma_3 t}$ (6)

Here, $D_{nm}$ is a coefficient determined by the initial condition, and $\gamma_{1,2,3}$ are eigenvalues of 3×3 coefficient matrix shown by Formula (5), and specifically have the following roots.

[Formula 7]

$$\gamma_{1,2} = \frac{Q \pm \sqrt{Q^2 - 4R}}{2}, \quad (7)$$

$\gamma_3 = 0$ $Q = -\left[\sigma_{01}I_p + (\sigma_f + \sigma_{12})I_e + \frac{1}{\tau} + k_{21} + k_{20}\right]$ $R = \left(\sigma_f I_e + \frac{1}{\tau}\right)(k_{20} - \sigma_{01}I_p) + k_{21}\left(\sigma_{01}I_p + \sigma_f I_e + \frac{1}{\tau}\right) + k_{20}(\sigma_{12}I_e + \sigma_{01}I_p)$ Therefore, Formula 6 can be rewritten as follows.

[Formula 8]

$n_0(t,I_e) = D_{11}e^{r_1 t} + D_{12}e^{r_2 t} + D_{13}$ $n_1(t,I_e) = D_{21}e^{r_1 t} + D_{22}e^{r_2 t} + D_{23}$, $n_2(t,I_e) = D_{31}e^{r_1 t} + D_{32}e^{r_2 t} + D_{33}$ (8)

The components of the exponential part of the Formula (8) indicate a transitional change in the population that occurs immediately after irradiation of the pump light and the erase light, and the other coefficients $D_{n3}$ indicate the populations of the respective states when the irradiation of light is continued and a steady state is achieved. Here, the roots $\gamma_{1,2}$ have negative values, showing the following relation.

[Formula 9]

$$\gamma_1 < \gamma_2 < -\frac{\left(\sigma_f I_e + \frac{1}{\tau}\right)(k_{20} - \sigma_{01}I_p) + k_{21}\left(\sigma_{01}I_p + \sigma_f I_e + \frac{1}{\tau}\right) + k_{20}(\sigma_{12}I_e + \sigma_{01}I_p)}{\sigma_{01}I_p + (\sigma_f + \sigma_{12})I_e + \frac{1}{\tau} + k_{21} + k_{20}} \quad (9)$$

Here, the inverse of $|\gamma_{1,2}|$ corresponds to the time when the transitional period is finished, and most molecules turn to the steady state within 1 nsec. Therefore, in most cases of fluorescence inhibiting processes using laser beam source of nanosecond order, the exponential terms of Formula (8) can be neglected so that Formula (8) can be rewritten as follows.

[Formula 10]

$n_0(t,I_e) \approx D_{13}$ $n_1(t,I_e) \approx D_{23}$, $n_2(t,I_e) \approx D_{33}$ (10)

Therefore, the population in $S_1$ state can be expressed more concretely as follows.

[Formula 11]

$$n_1(t, I_e) = \frac{\sigma_{01}I_p}{\frac{1}{\tau} + \sigma_{01}I_p + \left(\sigma_f + \sigma_{12}\frac{k_{20} + \sigma_{01}I_p}{k_{21} + k_{20}}\right)I_e}, \quad (11)$$

By substituting this Formula (11) to Formula (4), it is possible to calculate the dip ratio, which is important in the super-resolution microscopy.

[Formula 12]

$$P(I_e) = \frac{\frac{1}{\tau} + \sigma_{01}I_p}{\frac{1}{\tau} + \sigma_{01}I_p + \left(\sigma_f + \sigma_{12}\frac{k_{20} + \sigma_{01}I_p}{k_{21} + k_{20}}\right)I_e}, \quad (12)$$

For effectively inducing the fluorescence inhibition, the numerator of Formula (12) should preferably be as small as possible with reference to the denominator. In the case where the photon flux necessary for exciting the molecule from $S_0$ state to $S_1$ state is sufficiently small, Formula (12) can be approximated by even simpler Formula (13), as follows.

[Formula 13]

$$P(I_e) \approx \frac{\frac{1}{\tau}}{\frac{1}{\tau} + \left(\sigma_f + \sigma_{12}\frac{k_{20}}{k_{21} + k_{20}}\right)I_e}, \quad (13)$$

Here, paying particular attention to the denominator of Formula (13), and considering that $k_{20}/(k_{21}+k_{20})$ is a branching ratio for causing relaxation of the molecule from $S_n$ state through $S_1$ state, $\sigma_{12}k_{20}/(k_{21}+k_{20})$ can be interpreted as a cross-section for a non-radiative relaxation process after excitation from $S_1$ state to $S_n$ state. In addition, there is defined a spectral parameter ($\sigma_{dip}$) as expressed by the following Formula (14), i.e., a "dip cross-section". This parameter represents the total cross section relaxing from $S_1$ state except the area where the florescence process does not occur upon irradiation of the erase light, and is an important spectral parameter for determining the exhibition degree of the florescence inhibition, as well as the florescence life time $\tau$.

[Formula 14]

$$\sigma_{dip} = \sigma_f + \sigma_{12}\frac{k_{20}}{k_{21} + k_{20}} \quad (14)$$

As a light source of the super-resolution microscope, there are used commercial nanosecond pulse lasers having high versatility. These laser sources have pulse width of around 10 nsec. Therefore, from a practical viewpoint, microscope system can be developed using the relation of the dip ratio as expressed by Formula (14). Assuming that the optical system of the microscope is aplanatic, the logically expected PSF can be calculated by the following Formula (15) which is based on Formulas (1), (2), (3), (12) and (14).

[Formula 15]

$$F(r) = \frac{\frac{1}{\tau \varepsilon_p} C_{p0}}{\frac{1}{\tau} + 15.38 C_{e0} \frac{\sigma_{dip}}{\varepsilon_e} \left[\frac{2}{(k_e NAr)^2} \sum_{n=1}^{\infty} J_{2n+1}(k_e NAr) + \frac{1}{k_e NAr} J_2(k_e NAr)\right]^2} \left[\frac{2J_1(k_p NAr)}{k_p NAr}\right]^2, \quad (15)$$

Here, $\epsilon_p$ and $\epsilon_e$ represent the photon energy of the pump light and the erase light, respectively, and the photon flux can be calculated by dividing the irradiation intensity of the pump light or the ease light with the corresponding photon energy. In principle, by determining the irradiation conditions of the pump light and the erase light and determining the molecule of the sample, PSF of the super-resolution microscopy can be calculated using the Formula (15). However, from a practical viewpoint, Formula (15) can be more simplified by approximating it.

As can be appreciated from FIG. 5, a Bessel beam extends to a doubled seized range compared to a usual focused beam without spatial modulation. In addition, in practical use, as the erase light having longer wavelength bandwidth than that of the pump light is used for inhibiting the fluorescence caused by the irradiation of the erase light, the focusing size becomes even larger. Therefore, when the pump light and the erase light are coaxially focused on the sample surface, the majority of the intensity distribution of the pump light comes to exist inside the hole of the erase light. Consequently, by approximately expanding Formula (3) into power series of r around the vicinity of the optical axis, and approximating the intensity profile of the hole with simple function, the following Formula (16) can be obtained.

[Formula 16]

$$G(x) = 15.38 \frac{C_{e0}}{\varepsilon_e} \left[\frac{1}{6} k_e NAr - \frac{5}{385}(k_e NAr)^3 + O(r_5)\right]^2, \quad (16)$$

As can be appreciated from Formula (14), the terms of higher order not lower than $r^3$ are negligible as compared to the first term. In fact, the profile inside the hole can approximately be expressed by a quadratic function of r, as shown in FIG. 5. By using this result, Formula (15) can be simplified as the following Formula (17).

[Formula 17]

$$F(r) = \frac{\frac{1}{\tau} \frac{C_{p0}}{\varepsilon_p}}{\frac{1}{\tau} + \frac{\sigma_{dip} C_{e0}}{2.34 \varepsilon_e}(k_e NAr)^2} \left[\frac{2J_1(k_p NAr)}{k_p NAr}\right]^2, \quad (17)$$

Here, the Lorentzian function L(r) is defined by Formula (18).

[Formula 18]

$$L(r) = \frac{\frac{1}{\tau} \frac{C_{p0}}{\varepsilon_p}}{\frac{1}{\tau} + \frac{\sigma_{dip} C_{e0}}{2.34 \varepsilon_e}(k_e NAr)^2}, \quad (18)$$

Then, F(r) is nothing but the PSF of the pump light as modulated by the Lorentzian function L(r) of the half bandwidth (g) expressed by the following Formula (19).

[Formula 19]

$$g = 0.49 \sqrt{\frac{\varepsilon_e}{\tau \sigma_{dip} C_{e0}} \frac{\lambda_e}{NA}} \quad (19)$$

According to Formula (15), it can be appreciated that a half bandwidth (g) of PSF obtained by the super-resolution microscopy changes into a Lorentzian function as expressed by Formula (17) with the increase in the intensity of the erase light. Accordingly, it can be understood that, in order to make smaller the fluorescent spot as expressed by Formula (19), an essential qualification is to make $\sigma_{dip}C_{e0}$ larger. Particularly, in consideration of the practical utility, it is preferred for the intensity of the erase light to be as small as possible. It is thus advantageous to select, as a sample molecule, a molecule having a fluorescence lifetime τ and a dip cross-section, which are as large as possible.

Referring back to Formula (12), it is advantageous for effectively inducing the florescence inhibition that numerator of Formula (12) be as small as possible, with reference to the denominator. Generally, as the florescence lifetime τ is inherent to the sample molecule, it is inevitably required for the numerator of Formula (12) to satisfy the following condition: $\sigma_{01}$Ip≦(1/τ). In other words, the numerator must satisfy the following Formula (20).

[Formula 20]

$$\sigma_{01} I p \tau \leq 1 \qquad (20)$$

Moreover, with reference to Formula (17), in order to achieve an improved resolution in the super-resolution microscopy, it is necessary for the half bandwidth (g) of Lorentzian function, which is a modulating function expressed by Formula (18), to be smaller than the half bandwidth of the focusing beam size of the pump light as expressed by Formula (1). Here, by using the Rayleigh criterion, the half bandwidth (Γ) of the focused beam size of the pump light is generally expressed by the following Formula (21).

[Formula 21]

$$\Gamma = 0.61 \frac{\lambda_p}{NA}, \qquad (21)$$

Therefore, from Formulas (21) and (19), the condition for the half bandwidth (g) to be smaller than Γ is expressed by the following Formula (22).

[Formula 22]

$$0.49 \sqrt{\frac{\varepsilon_e}{\tau \sigma_{dip} C_{e0}}} \frac{\lambda_e}{NA} \leq 0.61 \frac{\lambda_p}{NA} \qquad (22)$$

More concretely, the condition is to satisfy the following Formula (23).

[Formula 23]

$$0.65(\lambda_e/\lambda_p) \leq \tau \sigma_{dip} I_e \qquad (23)$$

In addition, since it is preferred for the denominator of Formula (13) to be as large as possible with reference to its numerator, it is preferred for the photon flux of the erase light to satisfy the following Formula (24) using the dip cross-section, in consideration of τ that is inherent to the sample molecule.

[Formula 24]

$$\frac{1}{\tau} \leq \left(\sigma_f + \sigma_{12}\frac{k_{20}}{k_{21}+k_{20}}\right) I_e \qquad (24)$$

From Formula (24), the following Formula (25) can be obtained.

[Formula 25]

$$\tau \sigma_{dip} I_e \geq 1 \qquad (25)$$

From the above consideration, it can be concluded that the performance of the super-resolution microscope shown in FIG. 1 can be improved by configuring the microscope to satisfy the conditions of Formulas (20) and (23), and more preferably the condition of Formula (25).

In the next place, the super-resolution microscope shown in FIG. 1 will be further considered with reference to an experimental result, in which the wavelength of the pump light was 532 nm, the wavelength of the erase light was 599 nm, and rhodamine 6G was used as sample molecule. At first, the experimental data about the measurement of the dip ratio of rhodamine 6G in methanol solution was analyzed using Formula (13).

Figure 7:
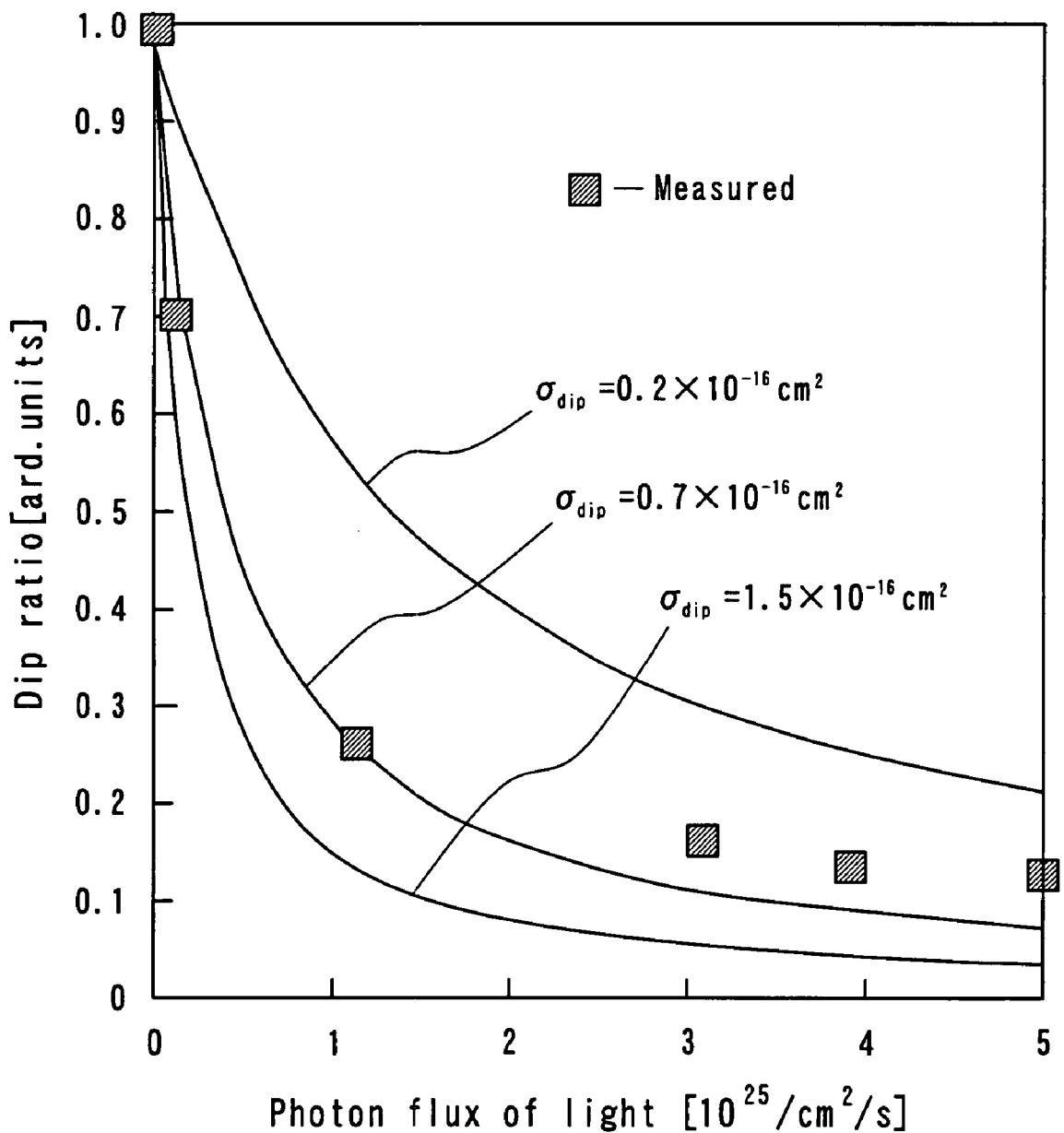
FIG. 7 shows a relation between the dip ratio and the photon flux of an erase light in the case where a rhodamine 6G is used.

FIG. 7 shows the relation between the dip ratio and the photon flux of the erase light, in which the dip ratio has, as a parameter, the dip cross-section ($\sigma_{dip}$) in case where the rhodamine 6G has a fluorescence lifetime τ of 3.75 nsec in the methanol solution. According to FIG. 7, it can be appreciated that the experimental result can substantially be reproduced by selecting $\sigma_{dip}$ around $0.7 \times 10^{-16}$ cm². An accurate value of $\sigma_{dip}$ of the rhodamine 6G is unclear because the absorption cross-section and the induced emission cross-section from $S_1$ state to the $S_n$ state are overlapped in the wavelength range of 599 nm. However, it is reported that the absorption cross-section and the induced emission cross-section from $S_1$ state to the $S_n$ state are in the order of $10^{-16}$ cm², so that the present analysis result can be evaluated to be validated.

Figure 8:
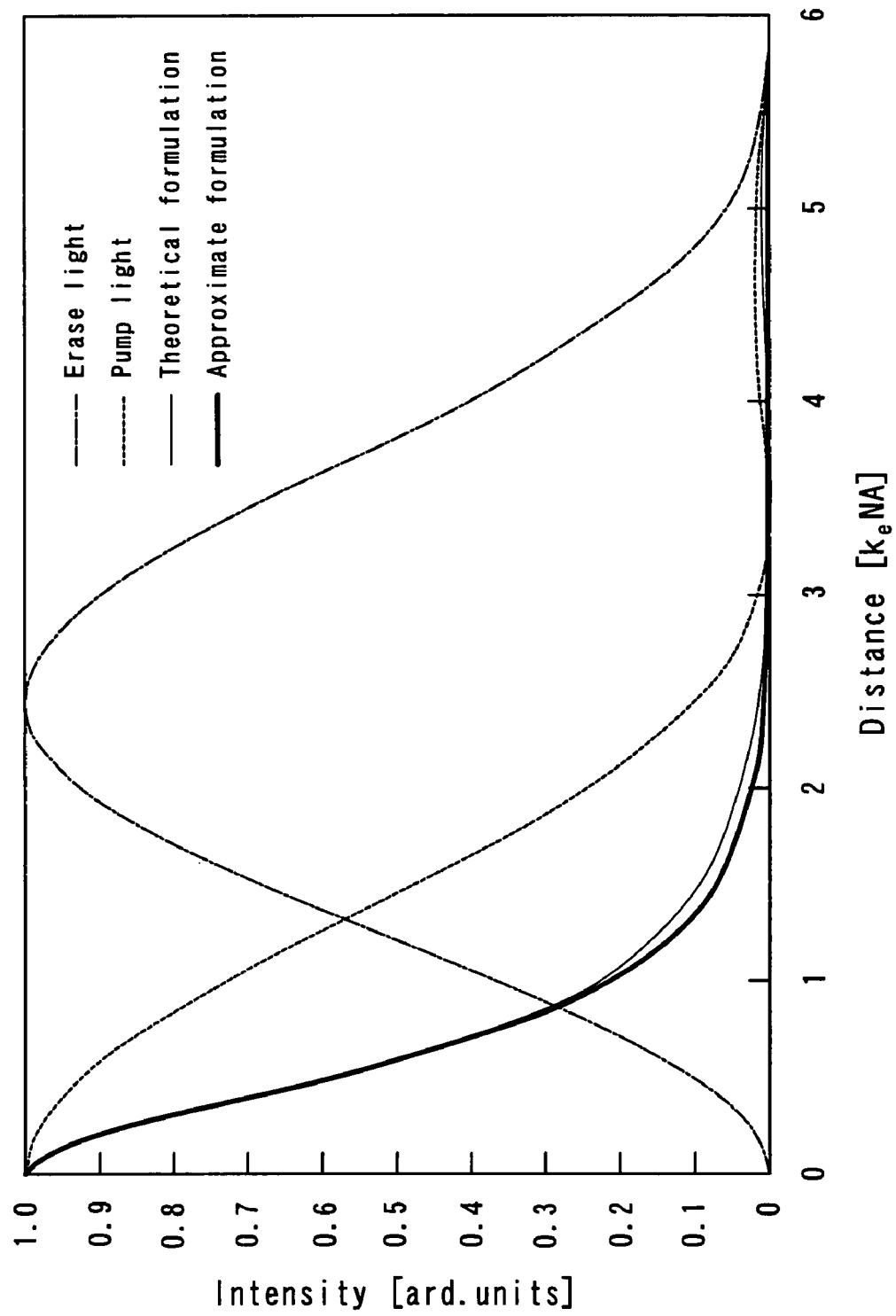
FIG. 8 is a graph showing a PSF in the case where the peak value of the photon flux of an erase light is $2.1 \times 10^{25}$ photons/sec/cm$^2$.

Subsequently, the present inventors calculated the PSF in super-resolution microscopy using Formula (15) and its approximated Formula (17), wherein $\sigma_{dip}$ and τ are assumed to be $0.7 \times 10^{-16}$ cm² and 3.75 nsec, respectively. FIG. 8 shows the PSF in case where the peak value of the photon flux of the erase light is $2.1 \times 10^{25}$ photons/sec/cm², i.e., the electric field intensity is 7 MW/cm². Heavy line and thin solid line in the figure represent the PSF of the Formulas (15) and (17), respectively. Although a slight desegregation appears around the sidelobe of the approximated formula, these profiles are adequately matched with each other. According to FIG. 8, a significant super-resolution occurs when the photon flux is on the order of $10^{25}$ photons/sec/cm². In the case of present calculation, the half bandwidth of the fluorescence profile contracts into 200 nm which is the ⅓ size of the diffraction limit of the pump light.

In consideration of the above-described conditions, if the photon flux Ip of the pump light is configured to be $10^{23}$ photons/cm²/sec, it is a sufficient light intensity for emitting fluorescence. For example, by applying the data as reported by E. Sahara and D. Treves, IEEE. J. Quantum Electron. 13, 962 (1997), in which $\sigma_{01}=4\times10^{-16}$ cm² and τ=3.75 nsec, the resultant $Ip\sigma_{01}\tau=0.15$ that satisfies Formula (20). In addition, by configuring as $Ie=10^{25}$ photons/cm²/sec and $\sigma_{dip}=0.6\times10^{-16}$ cm², the resultant $Ie\sigma_{dip}\tau=2.6$ that simultaneously satisfies Formulas (23) and (25), so that it is confirmed that the conditions as recited in the claims are actually satisfied.

Figure 9:
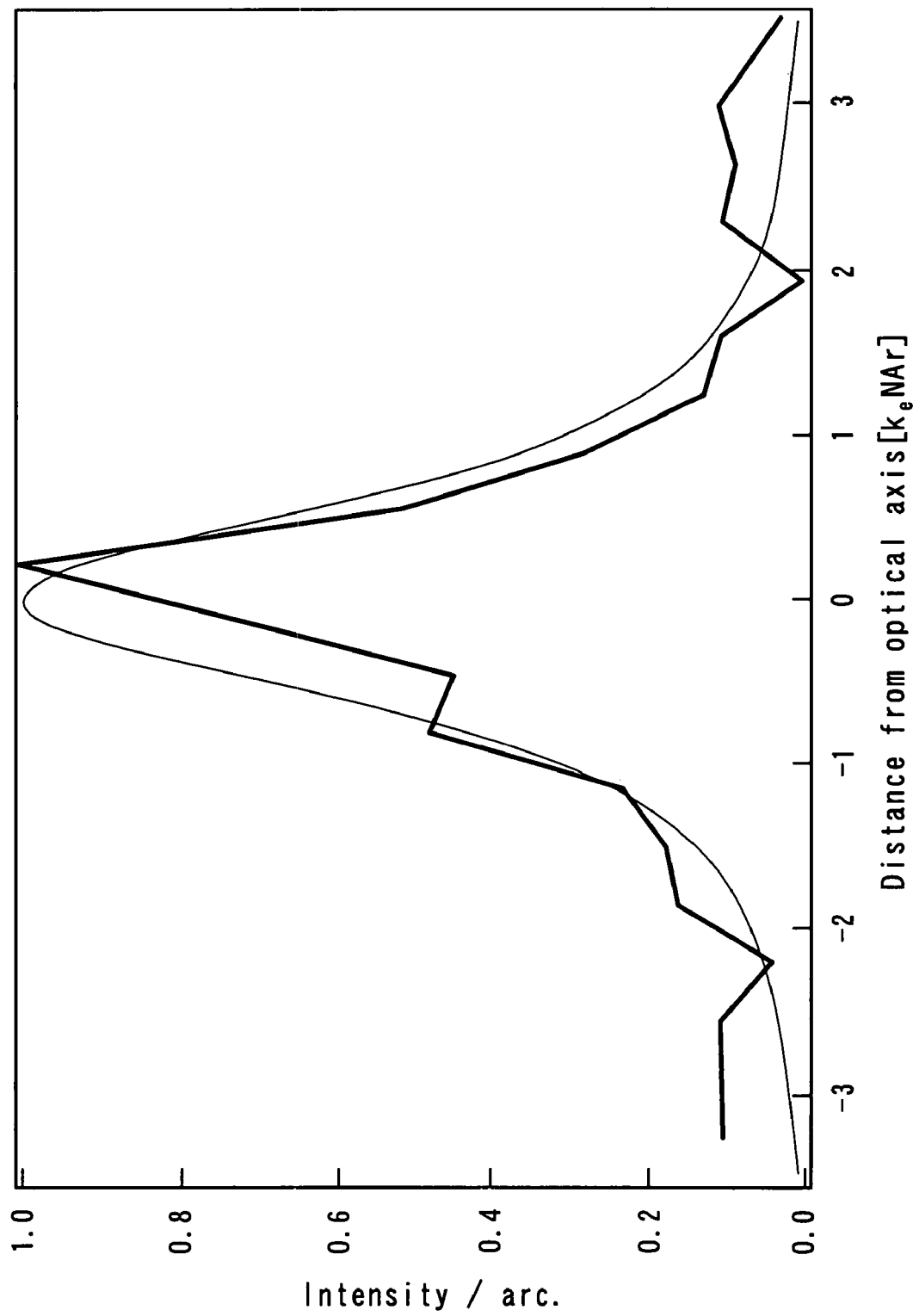
FIG. 9 is a graph showing a PSF in the case where an image of the fluorescence spot of a super-resolution microscopy is measured using a fluorescence beads of 175 μm in diameter.

FIG. 9 shows the PSF in case where the image of the fluorescence spot of the super-resolution microscopy is measured using a fluorescence beads of 175 μm in diameter in the same conditions. In FIG. 9, the measured profile shown in heavy line is also of Lorentzian type, having broadly extended side lobes as predicted by the theoretical analysis. Furthermore, the thin line in FIG. 9 shows the convolved result, in terms of the bead size, of the PSF as calculated from the theoretical formula obtained from FIG. 8. This theoretical calculation substantially exactly reproduces the experimental result. Consequently, it can be understood that the approximated Formula (17) is a reasonable function for expressing the PSF, as well as a practical formula based on a very clear physical model.

Figure 10:
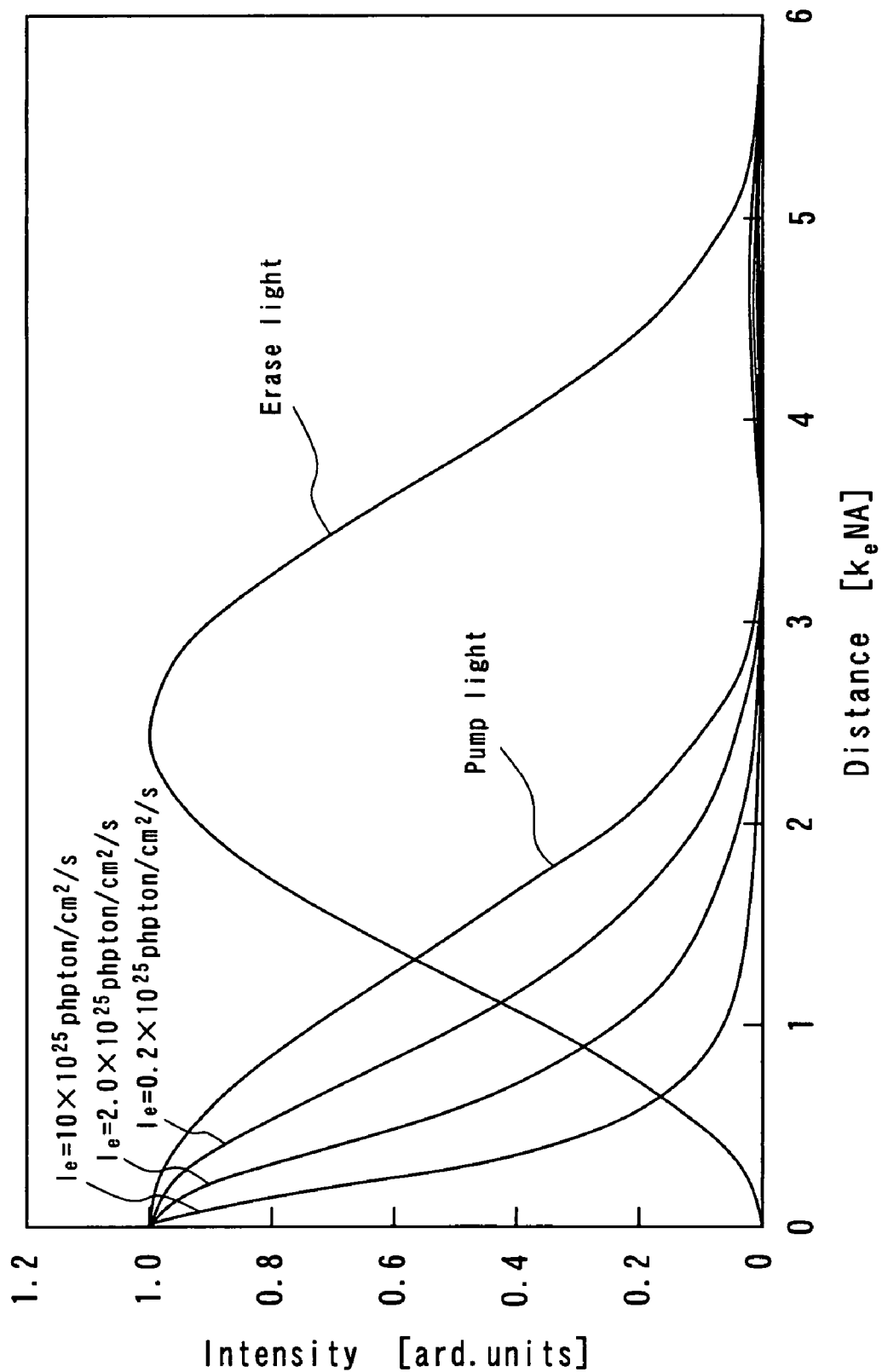
FIG. 10 shows a profile of the photon flux of an erase light.
Figure 11:
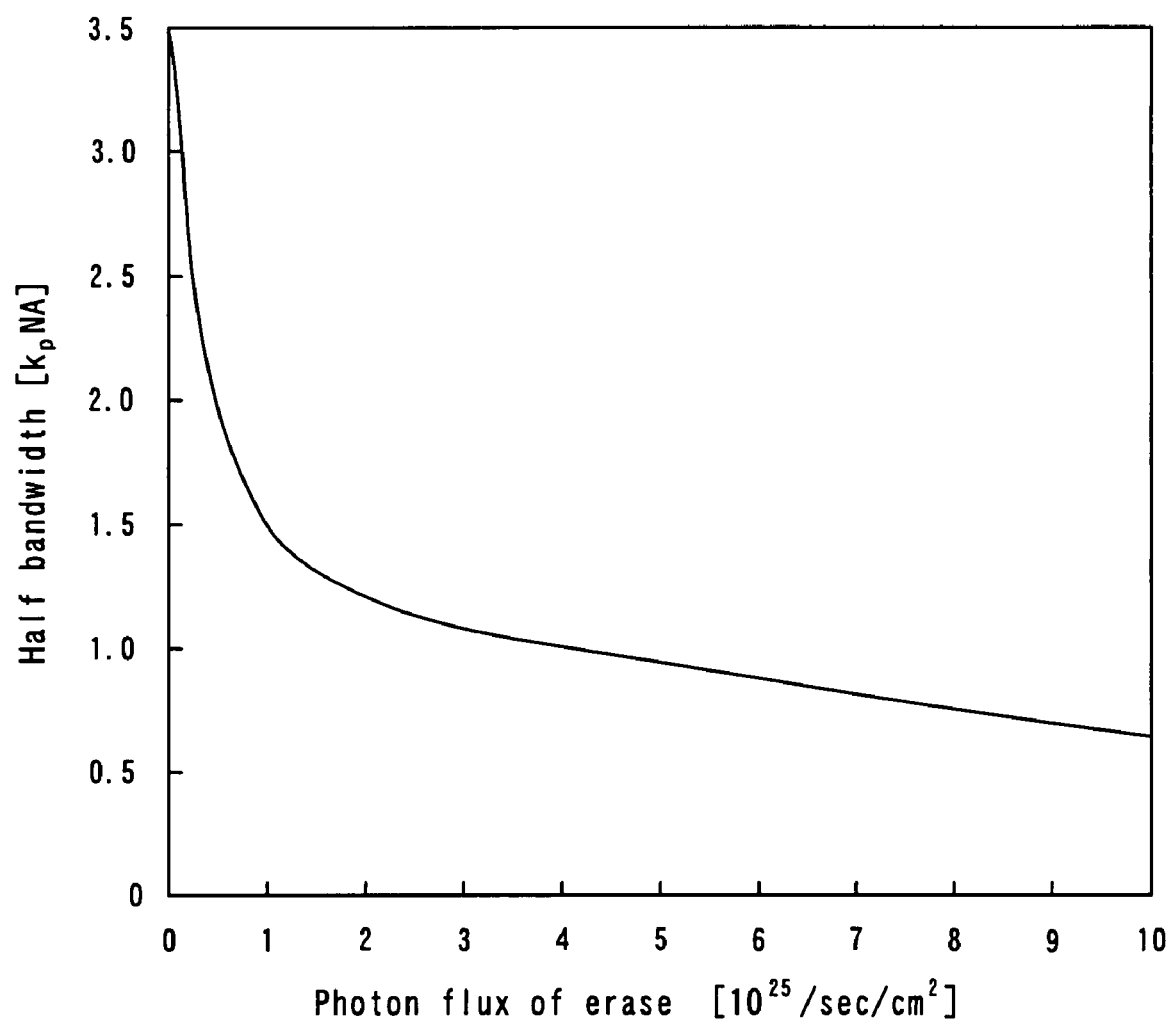
FIG. 11 shows a half bandwidth of the photon flux of FIG. 10.
Figure 12:
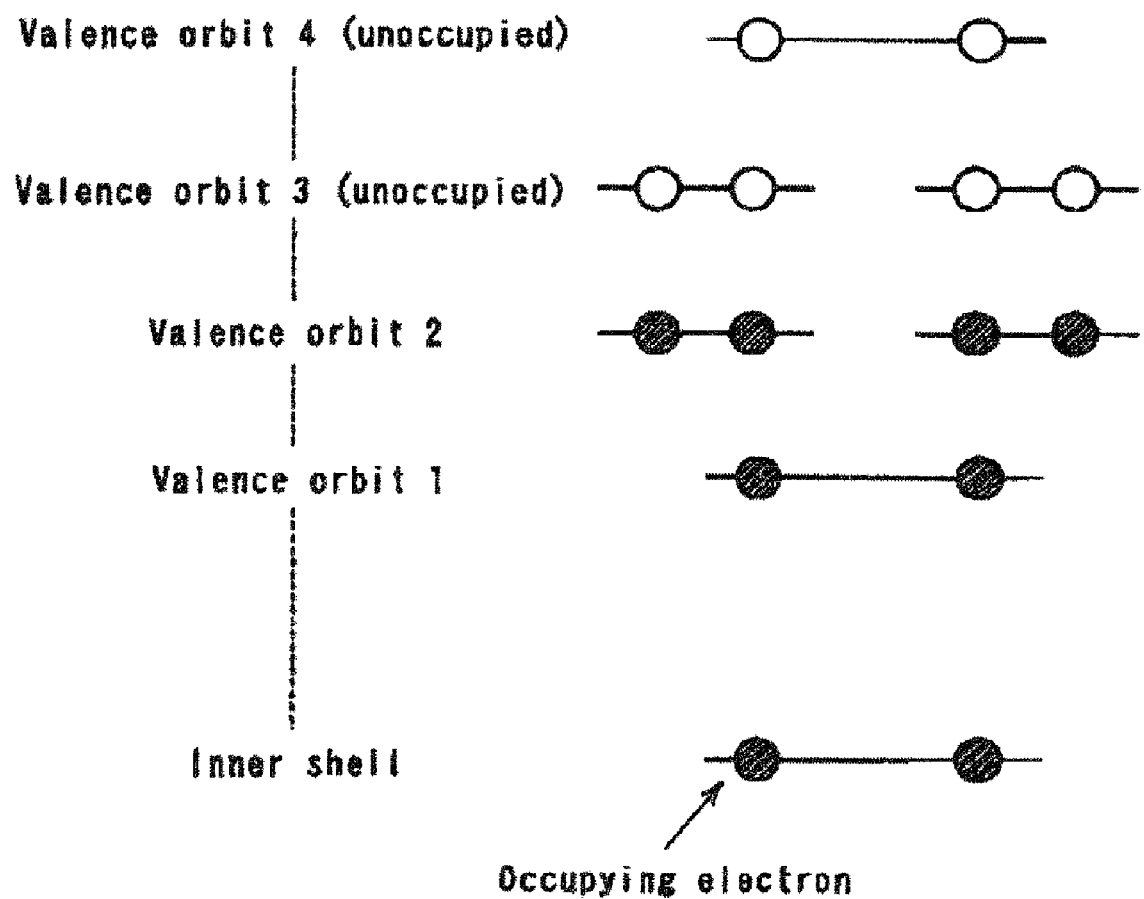
FIG. 12 is a diagram showing an electronic structure of valence orbits of a molecule contained in a sample.
Figure 13:
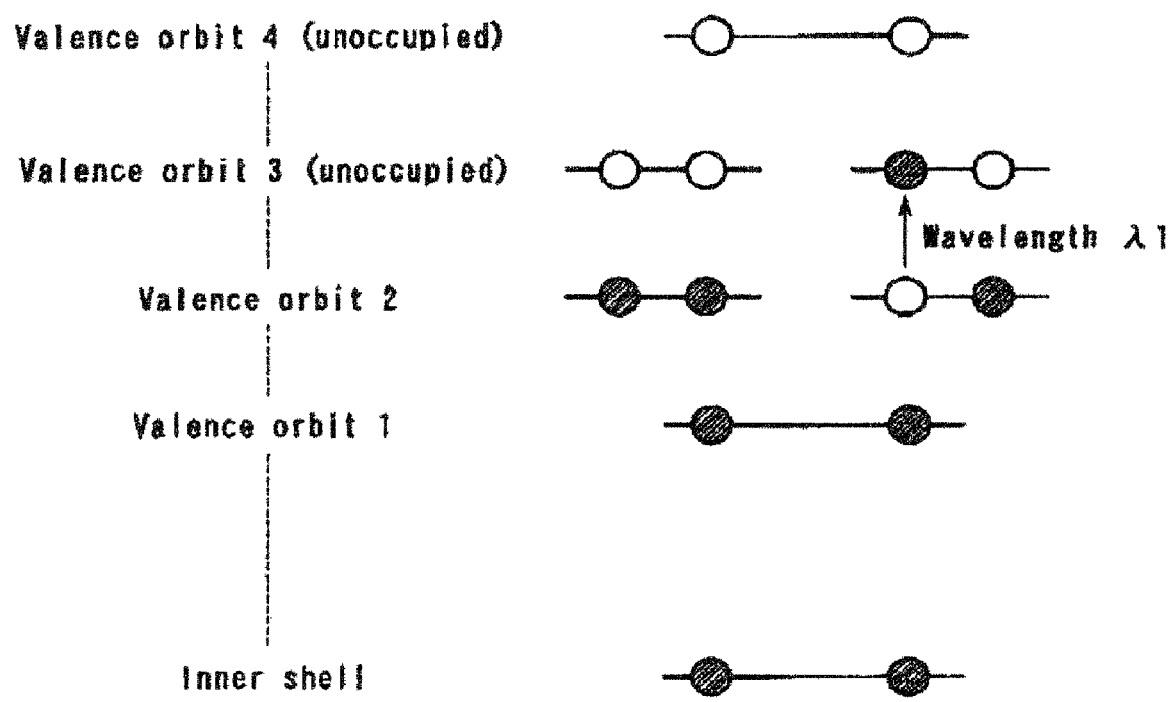
FIG. 13 schematically shows the molecule of FIG. 12 in the first electron-excited state.
Figure 14:
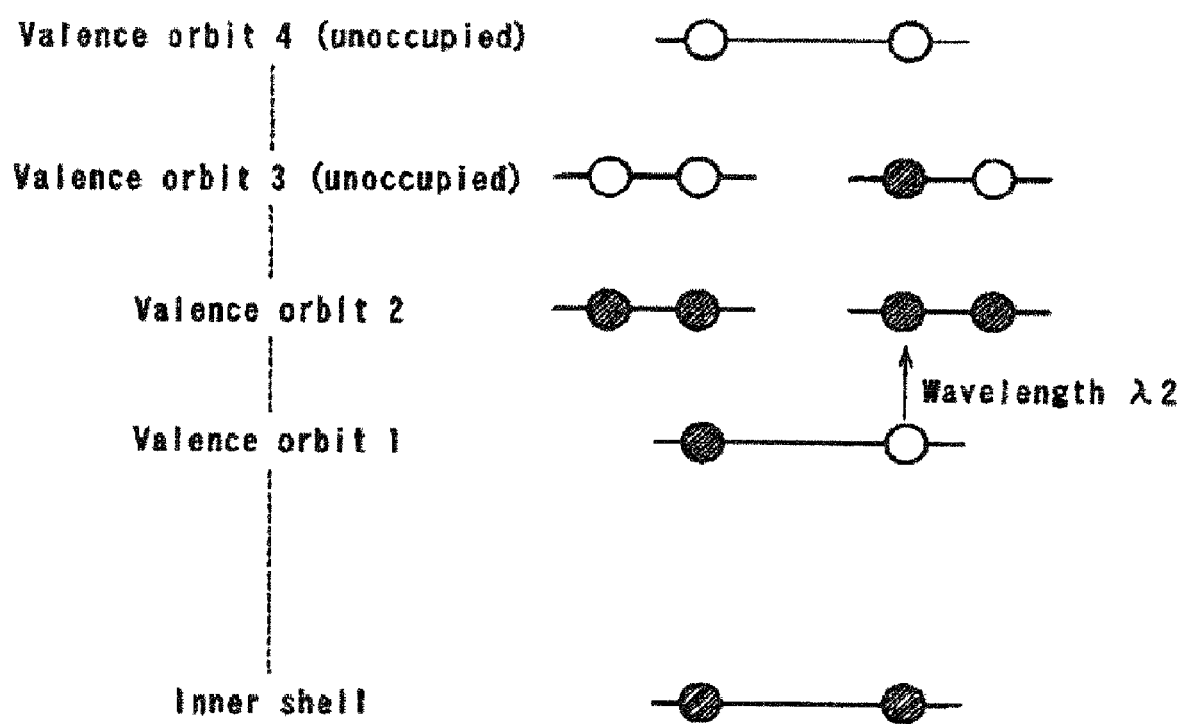
FIG. 14 also schematically shows the molecule of FIG. 12 in the second electron-excited state.
Figure 15:
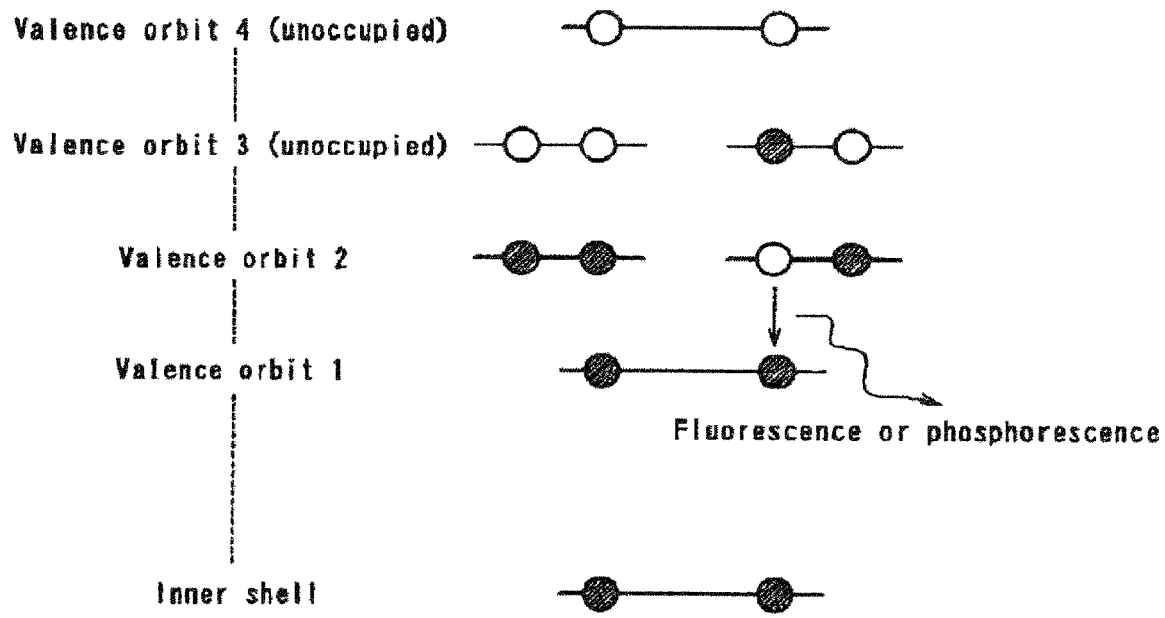
FIG. 15 also schematically shows a state wherein the molecule returns from the second electron-excited state to the ground state.
Figure 16:
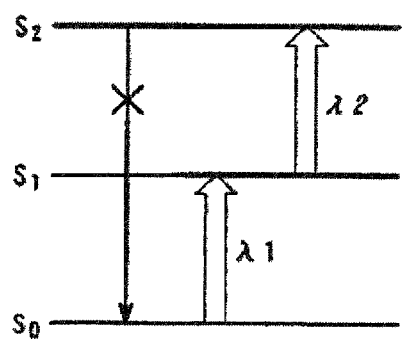
FIG. 16 is a schematic diagram for explaining the double resonance absorption process in a molecule.
Figure 17:
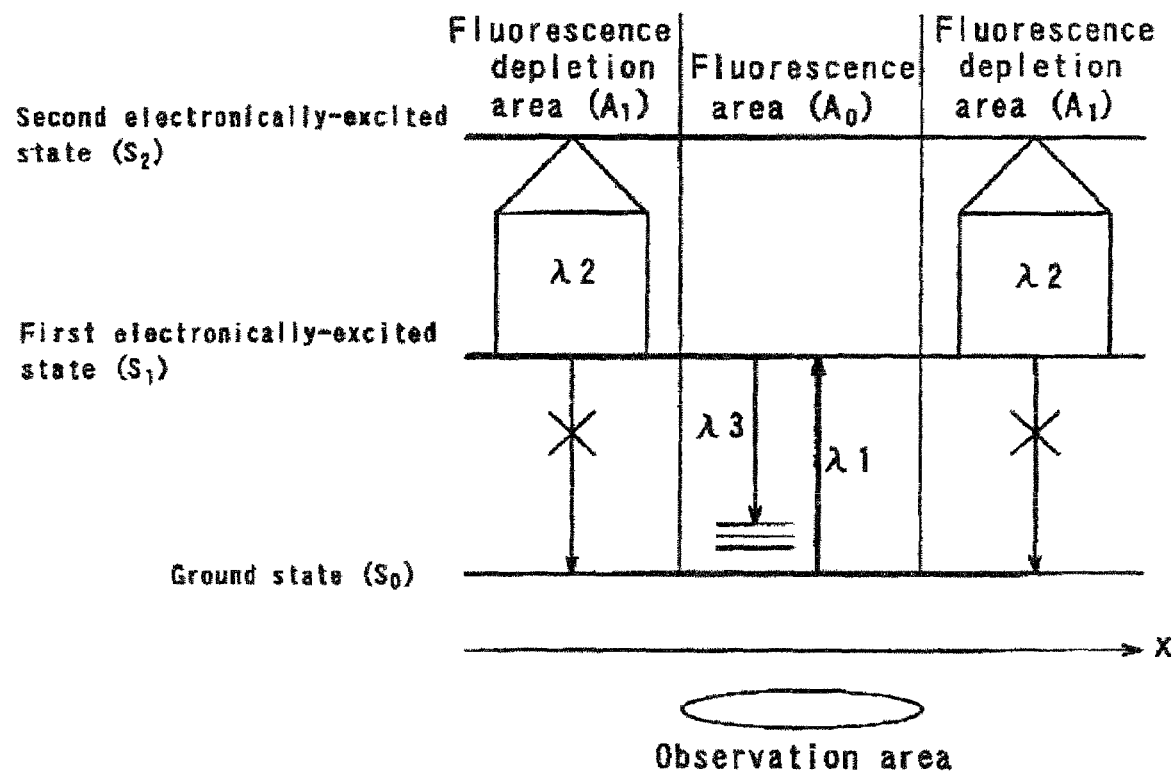
FIG. 17 is a schematic diagram for explaining the double resonance absorption process similar to FIG. 16.

Moreover, the relativity of the erase light on the photon flux has been calculated using Formula (17), for examining the imaging property of the PSF in case where rhodamine 6G is used. FIGS. 10 and 11 show the calculated profile and its half bandwidth, respectively. As can be appreciated from FIGS. 10 and 11, if the photon flux of the front value of the focused ease light is $5 \times 10^{25}$ photons/sec, the half bandwidth contracts to a size of ¼ of the diffraction limit. For example, when an oil-immersed objective lens having a numerical aperture of 1.4 is used, its half bandwidth is 70 nm, so that the spatial resolution beyond 100 nm can be expected, which had been impossible to realize with conventional optical microscopes. The time-averaged energy intensity of the erase light is calculated to be about 20 mW. This result indicates that a low output laser source can be used, so as to realize a microscope system with a simple configuration based on a reliable CW laser, without using a short-pulse laser source which is hard to handle. The fact that the microscope system can be realized with such a simple laser indicates the advantageous effects of the present invention involved with its practical application, such as cost reduction of the system, management of the wavefront of the laser that is unique to the present invention, etc.

INDUSTRIAL APPLICABILITY

The super-resolution microscope according to the present invention can be applied to observe a sample with a spatial resolution beyond the diffraction limit of the optical system.

The invention claimed is:

1. A super-resolution microscope comprising:
   a first light source for irradiating a first coherent light, with respect to a sample containing a molecule with at least three electronic states including a ground state, so as to excite the sample from the ground state to a first electron-excited state having an excited lifetime $\tau$;
   a second light source for irradiating a second coherent light to the sample so as to excite the sample from the first electron-excited state to a second electron-excited state having a higher energy level than the first electron-excited state;
   optical systems for combining a part of the first coherent light and a part of the second coherent light and focusing the coherent lights onto the sample;
   a scanning unit for scanning the sample by relatively moving the lights focused by the optical systems; and
   a detecting unit for detecting an optical response signal generated by the sample as a result of the irradiation from the optical systems;
   wherein the super-resolution microscope is configured so as to satisfy:

$\sigma_{01} I p \tau \leq 1$, and $0.65(\lambda e/\lambda p) \leq \tau \sigma_{dip} I e$ where $\lambda p$ is a wavelength of the first coherent light, $\lambda e$ is a wavelength of the second coherent light, $\tau$ is the excited lifetime in which the molecule is excited by the first coherent light from the ground state to the first electron-excited state, Ip is a maximum photon flux on a sample surface of the first coherent light, Ie is a maximum photon flux on a sample surface of the second coherent light, $\sigma_{01}$ is an absorption cross-sectional area when the molecule is exited from the ground state to the first electron-excited state, and $\sigma_{dip}$ is a fluorescence suppression cross-sectional area.

2. The super-resolution microscope according to claim 1, wherein the super-resolution microscope is configured so as to further satisfy:

$\tau \sigma_{dip} I e \geq 1$.

3. A super-resolution microscope according to claim 2, wherein $\sigma_{dip}$ is calculated by:

$\sigma_{dip} = \sigma_f + \sigma_{12}(k_{20}/k21 + k_{20})$, where $\sigma_f$ is an induced emission cross section when the molecule is relaxed from the first electron-excited state to the ground state, $\sigma_{12}$ is an absorption cross-sectional area when the molecule is excited from the first electron-excited state to the second electron-excited state, $k_{20}$ is a relaxation velocity from the second electron-excited state to the ground state, and $k_{21}$ is a relaxation velocity from the second electron-excited state to the first electron-excited state.

4. A super-resolution microscope according to claim 1, wherein σdip is calculated by:

$\sigma_{dip} = \sigma_f + \sigma_{12}(k_{20}/k2 + k_{20})$ where $\sigma_f$ is an induced emission cross section when the molecule is relaxed from the first electron-excited state to the ground state, $\sigma_{12}$ is an absorption cross-sectional area when the molecule is excited from the first electron-excited state to the second electron-excited state, $k_{20}$ is a relaxation velocity from the second electron-excited state to the ground state, and $k_{21}$ is a relaxation velocity from the second electron-excited state to the first electron-excited state.

* * * * *